United States Patent [19]

Gyovai et al.

[11] Patent Number: 4,949,711
[45] Date of Patent: Aug. 21, 1990

[54] DYNAMIC MP JOINT EXTENSION SPLINT

[75] Inventors: James E. Gyovai, Albany, Oreg.; Michael A. Jennings, San Jose; Mark E. Biehl, Campbell, both of Calif.

[73] Assignee: North Coast Medical, Inc., San Jose, Calif.

[21] Appl. No.: 321,630

[22] Filed: Mar. 8, 1989

[51] Int. Cl.$^5$ ............................ A61F 5/04; A61F 5/10
[52] U.S. Cl. .................................. 128/87 A; 128/77; 128/85; 128/87 R
[58] Field of Search ................ 128/77, 85, 87 A, 878, 128/879, 87 R

[56] References Cited

U.S. PATENT DOCUMENTS 3,903,878  9/1975  Spann ..................................... 128/77
4,602,620  7/1986  Marx ...................................... 128/77
4,765,320  8/1988  Lindemann et al. ............. 128/87 A

FOREIGN PATENT DOCUMENTS 2576512  8/1986  France ................................. 128/77

Primary Examiner—Robert A. Hafer
Assistant Examiner—Kerry Owens
Attorney, Agent, or Firm—Flehr, Hohbach, Test, Albritton & Herbert

[57] ABSTRACT

A low-profile dynamic hand splint including a rigging which is attached to a finger sling and which uses a single extendable coil spring to generate a variable tension force in the rigging. The tension force in the rigging is adjusted over a range of up to approximately 400 grams by attachment of one end of the rigging to various points on the base of the hand splint using releasable hook and loop fasteners. Use of a single extendable coil spring with an adjustable attachment point for the end of the rigging permits the rigging to be short in length and to be conveniently attached to the splint near a patient's wrist.

6 Claims, 3 Drawing Sheets

DYNAMIC MP JOINT EXTENSION SPLINT

BACKGROUND OF THE INVENTION

1. Field of the Invention.

This invention relates to an improved low-profile outrigger for use with a dorsal wrist splint and, more particularly, to an improved apparatus and method of adjusting the tension in the rigging thereof.

2. Prior Art.

Dynamic hand splints are used to provide dynamic forces to the digits of a hand. These splints are particularly useful for extension of the proximal interphalangeal joints. Dynamic hand splints are often used after implant resection arthroplasty of the metacarpophalangeal joints of a hand These type of splints are used for a number of purposes including: promotion of tissue synthesis, promotion of tendon gliding, assistance of the lymphatic pump, prevention and correction of deformity, increasing the range of motion, assistance to neurologic function, prevention of softer tissue adhesion, and protection for healing tissues. The amount of force applied varies. However, it is generally believed that the maximum force that should be used in dynamic splinting is approximately 300 grams. In prior art dynamic splints, the dynamic force is generated by rubber bands and colorcoded springs, which generate a specific force.

U.S. Pat. No. 4,765,320 by Lindemann et al. entitled "Dynamic Low Profile Splint" discloses a dynamic splint which has an outrigger structure mounted on a forearm piece. A key element disclosed by this patent is an elongated laterally adjustable "rigging guide" which is part of a pulley system mounted on the outrigger structure. The rigging guide operates as a pulley for changing the direction and the amount of force applied by a rigging to a finger sling. A fastening clamp for the rigging guide is rotated to vary the tension of the rigging. Tension is generated with an "elastic band." The rigging guide is an extra arm which extends distally from the outrigger structure over a finger and is adjustably mounted to vary the force on the rigging.

U.S. Pat. No. 4,602,620 entitled "Dynamic Outrigger Extension for Dorsal Wrist Splints," by Ralph Marx discloses an outrigger structure having a number of wheels mounted thereupon for guiding a rigging line attached to a finger sling. The outrigger structure has a rigging which includes a rubber band as a dynamic force member. The end of the rigging is attached to a fixed point on a forearm. Improvements to the outrigger structure disclosed in the Marx '620 patent include substitution of fixed-length springs for the rubber bands. To obtain a particular spring force, one particular type of spring is used. To obtain a different force, another type of spring having the same length but with a different characteristic is used because the attachment point for the rigging on the forearm is fixed. To identify the different types of springs, the springs are color-coded.

SUMMARY OF THE INVENTION

It is therefore an object of the invention to provide an improved low profile outrigger system in which a single spring member is used to provide a range of tension on a rigging.

It is another object of the invention to provide a rigging attachment point which is located near the wrist, thus shortening the length of the rigging and removing its point of attachment from the forearm.

It is another object of the invention to provide a point of attachment for a rigging which is moveable to provide different tension forces on the rigging as a function of the location of the attachment point of the rigging.

It is another object of the invention to provide a coil spring which is designed to fail if it exerts more than 400 grams force thus automatically protecting a patients finger from being overstressed.

In accordance with these and other objects of the invention, a method and apparatus as provided for an improved low-profile dynamic hand splint. An outrigger for guiding a rigging connected to a finger sling is dorsally fixed to the splint base. The splint base is typically made of low temperature thermoplastic material which is molded to embrace the wrist and forearm. The rigging includes a monofilament nylon line which is connected at one end to a finger sling and at the other end to one end of a calibrated coil spring. The other end of the coil spring is fastened to the splint base near a patient's wrist using a releasable fastener which is attached to the splint base in a number of positions to provide a number of tension forces on the rigging. This arrangement provides a rigging which is short and conveniently attached near a patient's wrist rather than up on the patient's forearm. In one embodiment of the invention the rigging is attached to the splint base by using releasable loop and hook fastener pairs with one being fixed to the splint base and the other attached to the end of the rigging. The fastener attached to the rigging is variable in its position of attachment to the splint to extend the coil spring to a predetermined length to provide accurate adjustment of the amount of tension force applied to the rigging The coil spring is designed to be stretched to provide up to approximately 400 grams of force to the rigging and fails if it is stretched much beyond that point.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

Figure 1:
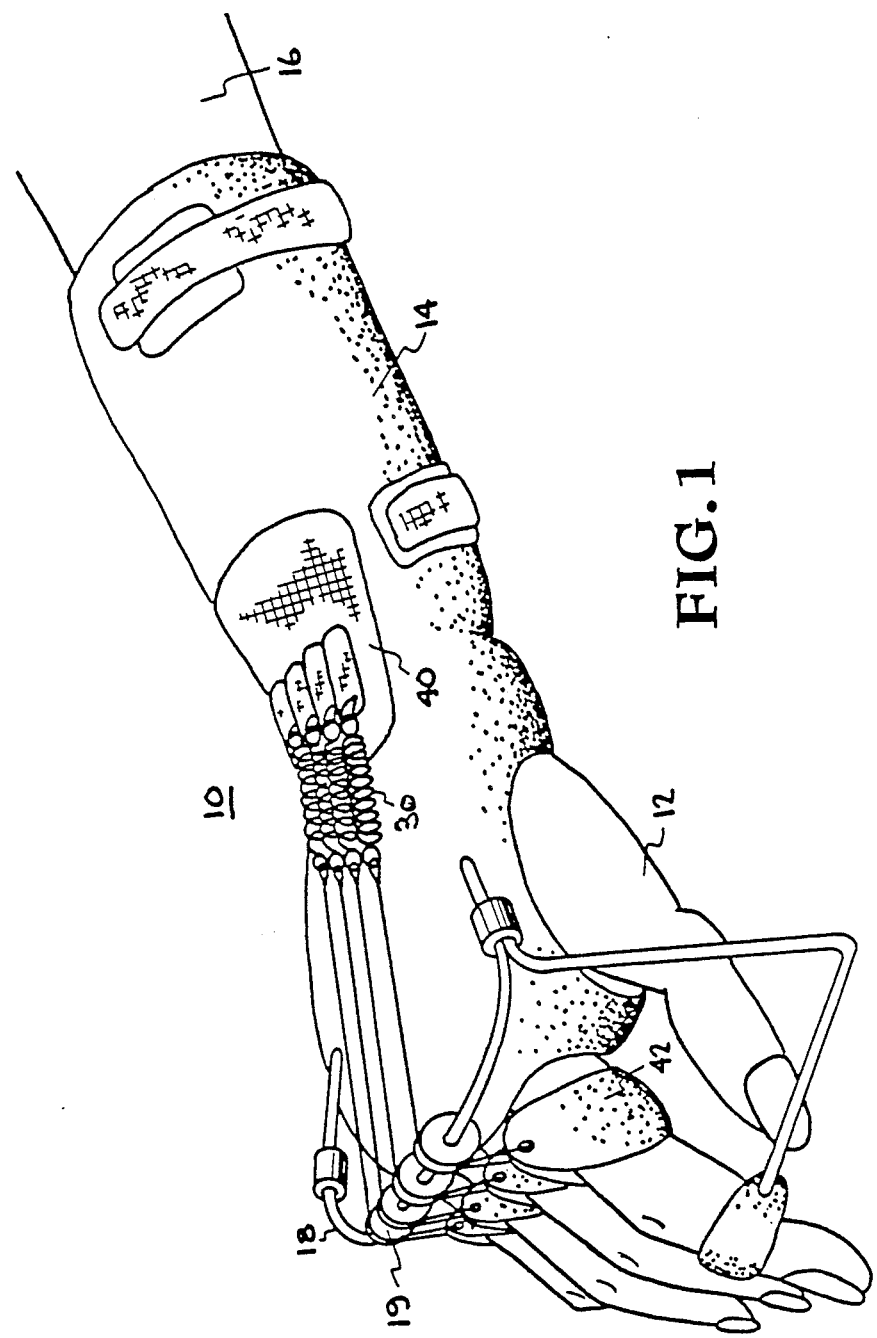
FIG. 1 is a perspective view of a low-profile dynamic splint system using an outrigger with a coil spring-biased rigging adjustably attached in the wrist area.

FIG. 1 shows a dynamic splint 10 for a hand 12. A splint base, or forearm piece, 14 of moldable, thermosetting setting material is formed around the hand 12 and forearm 16. An outrigger assembly 18, such as described in the Marx U.S. Pat. No. 4,602,620, is dorsally fixed to the distal end of the splint base 14. The proximal ends of the outrigger legs are fixed to the splint base 14 by bonding a piece of splint material to the splint base. The function of the outrigger assembly 18 and the wheels 19 mounted thereupon is to support and guide each of one or more riggings 20.

Figure 2:
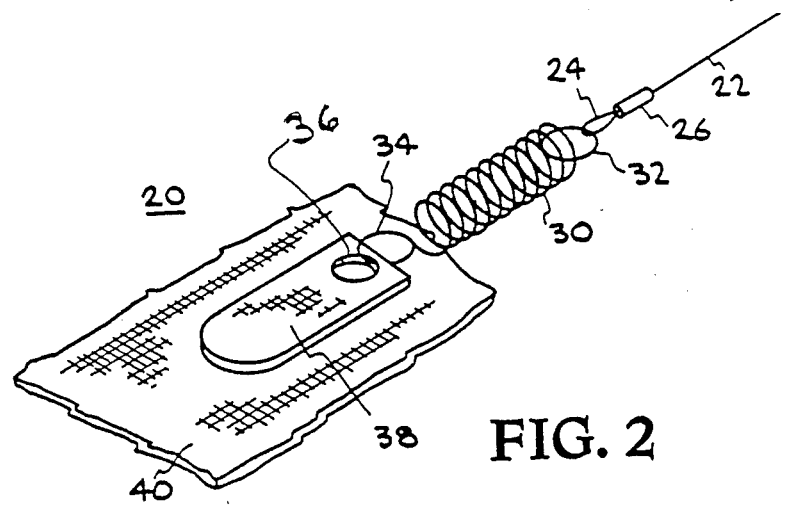
FIG. 2 is a view showing the details of a rigging according to the invention.

FIG. 2 shows a typical rigging 20 which includes a nylon monofilament line 22. A loop 24 is formed in one end of the line 22 using a crimp connector 26. Note that additional crimp connectors 26 on the line 22 may serve as a stop to limit the amount of travel of the line 22 by the crimp connector 26 engaging an outrigger wheel 19 as a stop.

A single stainless steel coil spring 30 is provided to be stretched to apply a predetermined amount of tension to the rigging when the rigging is in use in a dynamic splint. Two end loops 32,34 are formed at respective ends of the coil spring. The line loop 24 engages the spring loop 32. The spring is designed to provide a range of force as the spring is extended in length. For dynamic splinting applications, spring tension forces which range from 0–50 grams to 400 grams maximum are desirable. For a preferred embodiment of the invention, a spring is provided which provides 50 grams of tension when the spring is extended to a total length of one-inch with the length of the spring measured from one end loop to the other end loop. For every one-quarter of an inch extension, the spring is calibrated to provide an additional tension force of approximately 50 grams up to a maximum of 450 grams.

Figure 3:
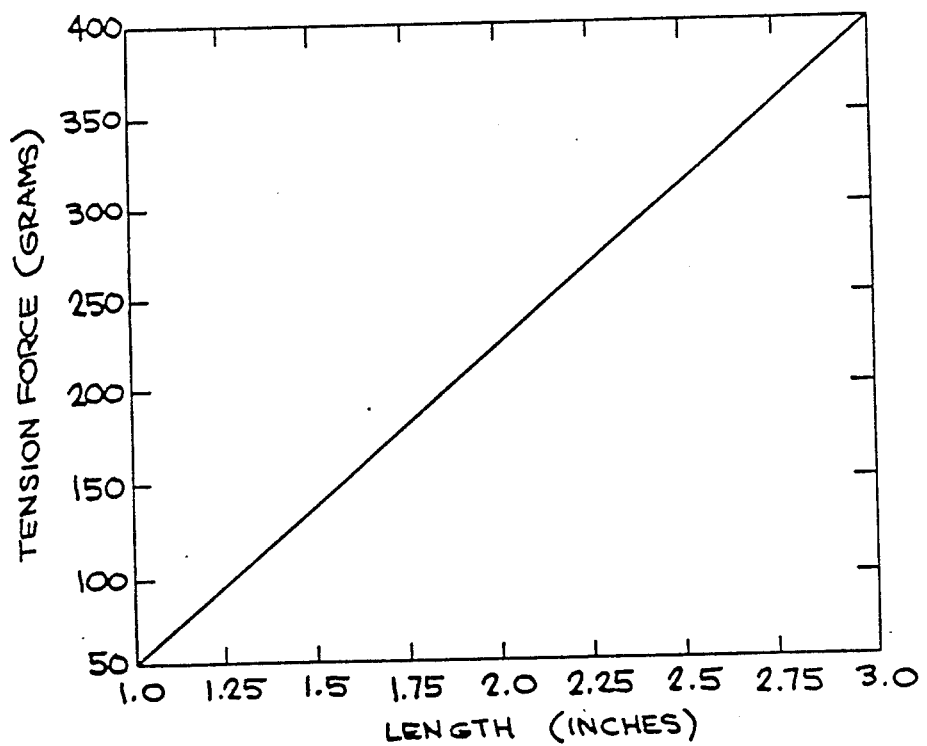
FIG. 3 is a chart showing tension versus displacement for a variable-tension spring used in the present invention.

FIG. 3 shows a graph of tension force exerted by the spring versus extension of the spring. The spring is designed to fail if it is stretched beyond three inches, so that the maximum tension that can be exerted is approximately 450 grams. The feature protects a finger from being overstressed.

Referring to FIGS. 2 and 3, the second loop 34 of the coil spring 30 engages a grommeted hole 36 formed at one end of an elongated, flexible strip 38 of pressure-sensitive loop material, such as provided commercially under the trademark Velcro. The strip is approximately ten millimeters wide by 30 millimeter long. The strip 38 releasably engages with a hook surface of a connection pad 40 which is attached to the splint base 14 near the wrist.

Tension on the rigging is accurately adjusted by positioning the strip 38 along the connection pad to stretch the coil spring 30 to a length which provides a required tension force for the rigging, in the range of 50 to 400 grams, as described hereinabove. The tension force in the line 22 is transmitted to the finger by means of a finger sling 42. The finger sling 42 is attached to the line 22 through a grommet which attaches the sides of the sling together and through which the line is attached to the sling by knotting or by crimping a loop in the end of the line.

Figure 4:
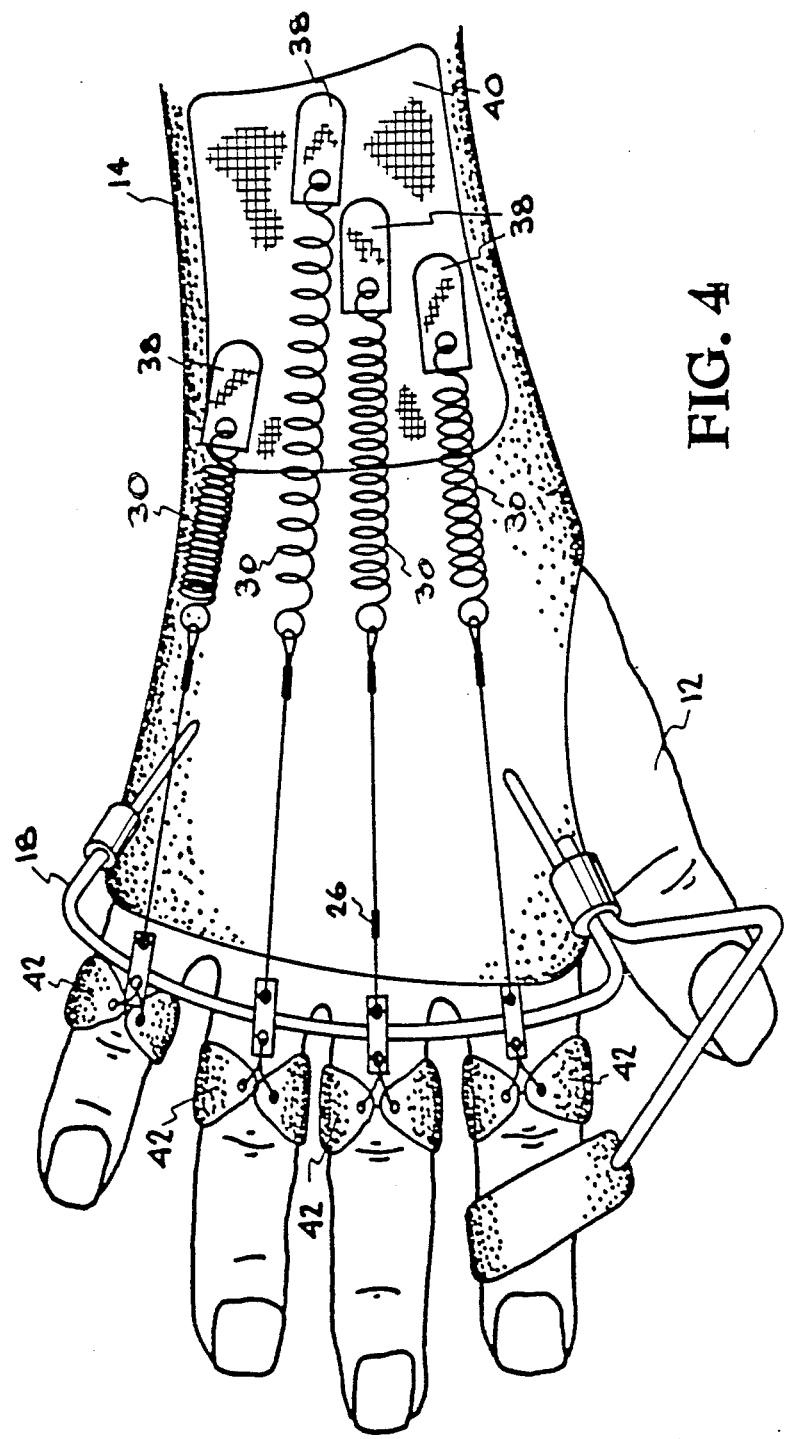
FIG. 4 is an enlarged plan view of the dynamic splint system according to the invention.

FIG. 4 shows in more detail the improved apparatus and operation provided by the invention. The invention eliminates the use of rubber bands and a number of different color-coded springs. It also provides accurate control of the amount of tension provided by the spring. Tension is controlled by controlling the amount of extension of the spring 30 by positioning the strip 38 on the connection pad 40 to obtain a predetermined amount of spring extension.

For example, in FIG. 4 the spring on the index finger rigging is extended 1½ inches to generate a tension force of 100 grams. The spring on the middle finger rigging is extended 2 inches to generate a tension force of 150 grams. The spring on the ring finger is extended 3 inches to generate a tension force of 400 grams. The spring on the little finger rigging is extended 1 inch to generate a tension force of 50 grams.

The combination of the line 22, spring 30, and fastener strip 38 provides a rigging which is compact and which is efficient. Because of this, the attachment point for the rigging to the splint base 14 can be moved from a point on the forearm to an area near the wrist. One obvious advantage of this is that the shorter riggings provided in accordance with the invention are attached to the splint base near the wrist to reduce interference with garments and arm coverings.

The invention permits a single spring to be used to generate the full range of tension forces required. This is accomplished by adjustment of the point of attachment of the rigging to the splint base 14. Because the spring is designed to fail when it is overstretched, excessive tension forces are prevented.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

We claim:

1. An improved low-profile dynamic splint for a hand, comprising:
   a splint base of moldable material for embracing a wrist and forearm, said splint base including an attachment area near a patient's wrist for adjustable attachment of a rigging to said splint base;
   an outrigger means fixed to said splint base for guiding a rigging connected to a finger loop means attached to one end of said rigging for engaging a finger;
   said rigging comprising:
      a line guided by said outrigger means and attached at one end to said finger loop means;
      coil spring means for applying a range of tension forces to said rigging, one end of said coil spring means attached to the other end of said line; and
      loop-and-hook means for releasably fastening a second end of said spring means to various points of said attachment area of said splint base near a patient's wrist to adjust the tension force provided by said coil spring means, wherein said releasable fastening means includes a detachable fastener element which is attached to said rigging and also includes a fastener pad which is fixed to said splint base for engaging said detachable fastener element, wherein said detachable fastener element includes a strip of fastening material which is releasably positionable at various points on said fastener pad to stretch said coil spring means to various lengths to provide corresponding tension forces to said rigging.

2. The dynamic splint of claim 1 wherein the coil spring means includes a calibrated coil spring which is stretched out to various lengths to provide a number of tension forces to said rigging.

3. The dynamic splint of claim 2 wherein the coil spring fails when it is stretched beyond a predetermined limit.

4. The dynamic splint of claim 1 wherein said coil spring exerts a tension force up to approximately 400 grams.

5. The dynamic splint of claim 1 wherein the rigging includes stop means fixed to said rigging for stopping flexure of a finger beyond a predetermined limit and wherein said stop means includes a stop member crimped to said rigging and engageable with a stop on said outrigger means.

6. A method of providing adjustable tensioning to a rigging of a dynamic hand splint, which includes a forearm piece, comprising the steps of:
   engaging a finger with a finger loop which is attached to a line portion of a rigging, said rigging including a coil spring for providing tension force to said rigging;
   guiding said line portion of said rigging through an outrigger means, which is fixed to said hand splint;
   releasable attaching one end of the rigging to the forearm piece near the wrist portion thereof by using hook-and-loop fastener means; and
   adjustably tensioning said rigging to exert a predetermined force by adjusting the position of attachment of one portion of the hook-and-loop fastener means to various positions on the forearm piece to stretch said spring to provide a predetermined tension force for said rigging.

* * * * *